US012734337B2

(12) United States Patent
Burkholz et al.

(10) Patent No.: US 12,734,337 B2
(45) Date of Patent: Sep. 15, 2026

(54) CATHETER SYSTEM WITH REMOTE INSTRUMENT DELIVERY

(71) Applicant: Becton, Dickinson and Company, Franklin Lakes, NJ (US)

(72) Inventors: Jonathan Karl Burkholz, Salt Lake City, UT (US); Bryan F. Bihlmaier, Provo, UT (US); Joseph Spataro, Cottonwood Heights, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/095,935

(22) Filed: Jan. 11, 2023

(65) Prior Publication Data

US 2023/0158276 A1 May 25, 2023

Related U.S. Application Data

(63) Continuation of application No. 16/385,873, filed on Apr. 16, 2019, now Pat. No. 11,571,550.

(Continued)

(51) Int. Cl.
*A61M 25/06* (2006.01)
*A61B 5/15* (2006.01)
*A61M 25/00* (2006.01)

(52) U.S. Cl.
CPC ... *A61M 25/0606* (2013.01); *A61B 5/150992* (2013.01); *A61M 25/0637* (2013.01); *A61M 25/0017* (2013.01); *A61M 25/0043* (2013.01)

(58) Field of Classification Search
CPC .......... A61M 25/0606; A61M 25/0637; A61M 25/0017; A61M 25/0043; A61M 25/0097;

(Continued)

(56) References Cited

U.S. PATENT DOCUMENTS 3,046,984 A * 7/1962 Eby ...................... A61M 25/02 128/DIG. 26
4,954,129 A * 9/1990 Giuliani ........... A61M 25/0017 604/93.01

(Continued)

FOREIGN PATENT DOCUMENTS

AU 2011302463 A1 4/2013
EP 1075299 B1 8/2004

(Continued)

*Primary Examiner* — Tasnim Mehjabin Ahmed

(74) *Attorney, Agent, or Firm* — Kirton McConkie; Whitney Blair; Kevin Stinger

(57) ABSTRACT

In some embodiments, a catheter system may include a catheter adapter having a distal end, a proximal end, and a lumen extending there between. In some embodiments, the catheter system may also include a catheter extending distally from the distal end of the catheter adapter, an extension tube, and a connector coupled to a proximal end of the extension tube. In some embodiments, a distal end of the extension tube may be coupled to the proximal end of the catheter adapter. In some embodiments, the connector, the extension tube, the lumen, and the catheter may form a straight pathway for delivery of an instrument to the catheter system. In some embodiments, an extension set for a catheter assembly may include the extension tube, the connector coupled to the proximal end of the extension tube, and another connector coupled to the distal end of the extension tube.

14 Claims, 13 Drawing Sheets

Related U.S. Application Data

(60) Provisional application No. 62/660,630, filed on Apr. 20, 2018.

(58) Field of Classification Search
CPC .... A61M 2025/024; A61M 2025/0266; A61M 2025/028; A61M 39/10; A61M 25/02; A61M 39/0247; A61M 2039/0258; A61B 5/150992
See application file for complete search history.

(56) References Cited

U.S. PATENT DOCUMENTS

| | | | | |
|---|---|---|---|---|
| 9,789,280 | B2 | 10/2017 | Ma | |
| 11,571,550 | B2 | 2/2023 | Burkholz et al. | |
| 2004/0102736 | A1* | 5/2004 | Bierman | A61M 25/02 604/180 |
| 2004/0127853 | A1 | 7/2004 | Howell | |
| 2004/0127854 | A1* | 7/2004 | Leinsing | A61M 39/26 604/167.03 |
| 2005/0015048 | A1 | 1/2005 | Chiu et al. | |
| 2006/0015086 | A1 | 1/2006 | Rasmussen et al. | |
| 2011/0160663 | A1 | 6/2011 | Stout et al. | |
| 2012/0016312 | A1 | 1/2012 | Brown et al. | |
| 2012/0053523 | A1 | 3/2012 | Harding | |
| 2014/0228775 | A1 | 8/2014 | Burkholz et al. | |
| 2014/0364766 | A1 | 12/2014 | Devgon et al. | |
| 2014/0364809 | A1 | 12/2014 | Isaacson et al. | |
| 2016/0106959 | A1 | 4/2016 | Woehr | |
| 2016/0317799 | A1* | 11/2016 | Tohse | A61B 17/12186 |
| 2017/0120001 | A1 | 5/2017 | Hyer et al. | |
| 2017/0120014 | A1 | 5/2017 | Harding et al. | |
| 2018/0154112 | A1* | 6/2018 | Chan | A61M 25/0606 |
| 2018/0317830 | A1 | 11/2018 | Devgon | |
| 2019/0038871 | A1* | 2/2019 | Beasley | A61M 25/01 |

FOREIGN PATENT DOCUMENTS

| | | | | |
|---|---|---|---|---|
| EP | 2972243 | A1 | 1/2016 | |
| GB | 2508466 | A | 6/2014 | |
| JP | H0286250 | A | 3/1990 | |
| JP | H0444947 | A | 2/1992 | |
| JP | 2010517640 | A | 5/2010 | |
| JP | 2013534455 | A | 9/2013 | |
| JP | 2013538620 | A | 10/2013 | |
| JP | 2015136524 | A | 7/2015 | |
| JP | 2016043201 | A | 4/2016 | |
| WO | 2012031145 | A1 | 3/2012 | |
| WO | WO-2016033143 | A1 * | 3/2016 | A61B 5/15003 |
| WO | 2017127074 | A1 | 7/2017 | |

* cited by examiner 70
66
30
68
41
16
16
24
12
14
22
20
52
42

70
68
66

CATHETER SYSTEM WITH REMOTE INSTRUMENT DELIVERY

RELATED APPLICATIONS

This application is a continuation of U.S. patent application Ser. No. 16/385,873, filed Apr. 16, 2019, entitled CATHETER SYSTEM WITH REMOTE INSTRUMENT DELIVERY, which claims priority to U.S. Provisional Patent Application No. 62/660,630, filed Apr. 20, 2018, entitled CATHETER SYSTEM WITH REMOTE INSTRUMENT DELIVERY, which are incorporated herein in their entirety.

BACKGROUND

Infusion therapy, a common healthcare procedure, may be facilitated by a vascular access device. Hospitalized, home care, and other patients receive fluids, pharmaceuticals, and blood products via a vascular access device inserted into the vascular system. Blood withdrawal is another common healthcare procedure that may be facilitated by a vascular access device.

A vascular access device may access a peripheral or central vasculature of a patient. A vascular access device may be indwelling for short term (days), moderate term (weeks), or long term (months to years). A vascular access device may be used for continuous infusion therapy or for intermittent therapy.

A common type vascular access device is an over-the-needle peripheral intravenous catheter (PIVC). As its name implies, the "over-the-needle" PIVC may be mounted over an introducer needle having a sharp distal tip. The sharp distal tip may be used to pierce skin and the vasculature of the patient. Insertion of the PIVC into the vasculature may follow the piercing of the vasculature by the needle. The needle and the PIVC are generally inserted at a shallow angle through the skin into the vasculature of the patient with a bevel of the needle facing away from the skin of the patient. Once placement of the needle within the vasculature has been confirmed, a clinician may temporarily occlude flow in the vasculature and withdraw the needle, leaving the PIVC in place for future fluid infusion and/or blood withdrawal.

Currently, there may be several limitations to the use of a PIVC for fluid infusion or blood draw. The PIVC may narrow, collapse, or clog with time, leading to failure of the PIVC. Also, blood extracted from PIVCs may often need to be discarded due to concerns regarding sample quality. Further, use of a PIVC to draw blood can be slow and somewhat inefficient, particularly when the patient as difficult intravenous access or veins that are not readily accessed by the clinician.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access systems, devices, and related methods. More particularly, in some embodiments, the present disclosure relates to catheter systems, devices, and related methods that may facilitate delivery of an instrument into an indwelling catheter and/or vasculature of a patient. In some embodiments, the instrument may include a guidewire, a probe with a sensor, tubing for fluid infusion or blood draw, a light tube for disinfection, or another suitable instrument. In some embodiments, the delivery of the instrument may be stabilized via one or more stabilization platforms or features. In some embodiments, the delivery of the instrument may occur through a straight pathway, which may facilitate support of the instrument and/or prevent bending of the instrument. In some embodiments, insertion of the instrument into the catheter may occur remotely, which may reduce interference with a catheter insertion site in the skin of the patient.

In some embodiments, the instrument may include tubing, and the delivery of the instrument into the catheter and/or the vasculature of the patient may allow a user to draw a blood sample or infuse fluid through the catheter when the catheter is no longer functional or effective for blood collection due to, for example, debris build up on a distal end of the catheter or collapse of the catheter. Thus, in some embodiments, the delivery of the instrument into the catheter may reduce a number of needle sticks that a patient experiences as the second catheter may be replaced less frequently.

In some embodiments, a catheter system may include a catheter adapter having a distal end, a proximal end, and a lumen extending between the distal end and the proximal end. In some embodiments, the proximal end of the catheter adapter may be axially aligned with the distal end of the catheter adapter. In some embodiments, the catheter system may include a catheter, which may extend distally from the distal end of the catheter adapter. In some embodiments, the catheter may include a PIVC.

In some embodiments, the catheter system may include an extension tube, which may include a distal end and a proximal end. In some embodiments, the distal end of the extension tube may be coupled to the proximal end of the catheter adapter. In some embodiments, the catheter system may include a connector coupled to the proximal end of the extension tube. In some embodiments, the connector, the extension tube, the lumen, and the catheter may form the straight or linear pathway for delivery of the instrument to the catheter system. In some embodiments, the instrument may be delivered through the catheter system into the vasculature of the patient.

In some embodiments, the distal end of the extension tube may be coupled to the proximal end of the catheter adapter via a luer adapter. In some embodiments, the luer adapter may be selectively coupled to a corresponding luer adapter disposed on the proximal end of the catheter adapter. In some embodiments, the distal end of the extension tube may be fixedly coupled to the proximal end of the catheter adapter. In some embodiments, the extension tube may allow remote delivery of the instrument, which may decrease disturbance of an insertion site of the catheter.

In some embodiments, the extension tube may be rigid, semi-rigid, or flexible. In some embodiments, the extension tube may include a durometer between 70 Shore A and 95 Shore A, inclusive. In some embodiments, the extension tube may be a first extension tube. In some embodiments, the catheter system may include second extension tube coupled to the first extension tube. In some embodiments, the second extension tube may be disposed at an angle with respect to the first extension tube. In some embodiments, a hardness of the first extension tube may be greater than a hardness of the second extension tube.

In some embodiments, the connector may include a Y-adapter, which may include a first port and a second port. In some embodiments, the first port may be configured to couple with an instrument delivery device. In some embodiments, the second extension tube may extend from a second port of the Y-adapter. In some embodiments, the connector may include a blood control septum.

In some embodiments, the catheter system may include at least one stabilization feature, which may be disposed between the connector and the distal end of the extension tube. In some embodiments, the extension tube may extend through the stabilization feature. In some embodiments, the stabilization feature may be fixed with respect to the extension tube. In some embodiments, the stabilization feature may rotate on the extension tube about a longitudinal axis of the extension tube.

In some embodiments, the stabilization feature may include one or more platforms, which may include an adhesive layer. In some embodiments, the adhesive layer may be configured to contact skin of a patient. In some embodiments, the catheter system may include securement fabric, which may be coupled to the stabilization feature. In some embodiments, the fabric may extend outwardly from the stabilization feature. In some embodiments, the fabric may include an adhesive layer, which may be configured to contact the skin of the patient.

In some embodiments, a catheter assembly may include the catheter adapter and the catheter. In some embodiments, an extension set for the catheter assembly may include the extension tube, the connector coupled to the proximal end of the extension tube, and another connector coupled to the distal end of the extension tube. The extension tube, the connector, and the other connector may form at least a portion of the straight pathway. In some embodiments, the straight pathway may align with a longitudinal axis of the catheter assembly.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

The present disclosure relates generally to vascular access systems, devices, and related methods. More particularly, in some embodiments, the present disclosure relates to catheter systems, devices, and related methods to facilitate delivery of an instrument into a particular catheter system and/or vasculature of a patient.

Figure 1A:
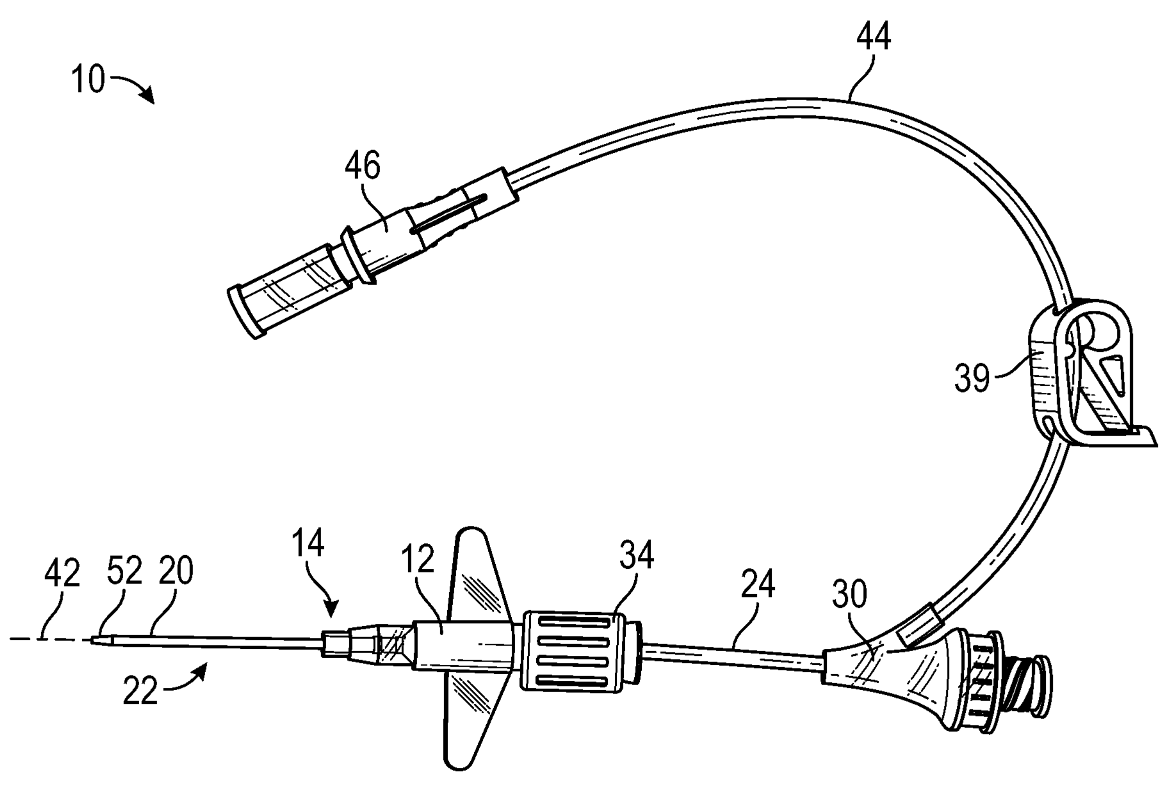
FIG. 1A is an upper perspective view of an example catheter system, according to some embodiments.
Figure 1B:
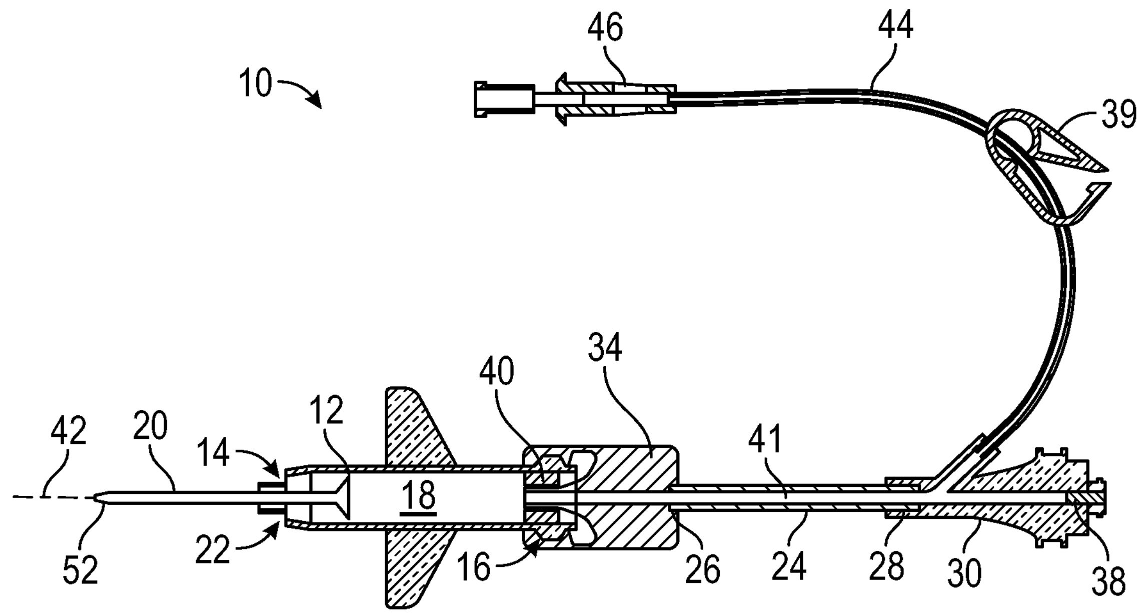
FIG. 1B is a cross-sectional view of the catheter system of FIG. 1A, according to some embodiments.

Referring now to FIGS. 1A-1B, in some embodiments, a catheter system 10 may include a catheter adapter 12 having a distal end 14, a proximal end 16 axially aligned with the distal end 14, and a lumen 18 extending between the distal end 14 and the proximal end 16. In some embodiments, the catheter system 10 may include a catheter 20, which may extend distally from the distal end 14 of the catheter adapter 12. In some embodiments, a catheter assembly 22 may include the catheter adapter 12 and the catheter 20. In some embodiments, the catheter 20 may include a PIVC.

In some embodiments, the catheter system 10 may include an extension tube 24, which may include a distal end 26 and a proximal end 28. In some embodiments, the catheter system 10 may include a connector 30 coupled to the proximal end 28 of the extension tube 24. In some embodiments, the connector 30 may be configured to connect an instrument delivery device to the catheter system 10. In some embodiments, the connector 30 may selectively couple the instrument delivery device to the catheter system

10 such that the instrument delivery device may be removed from the catheter system 10. In some embodiments, the connector 30 may include a luer adapter, such as a male or female luer adapter, or any other suitable connector. In some embodiments, the connector 30 may be a luer-activated needleless connector or a non-luer activated needleless connector. In some embodiments, the connector 30 may include a SMARTSITE™ Needle-Free Connector available from Becton, Dickinson and Company, a Q-SYTE™ Luer Activated Split Septum available from Becton, Dickinson and Company, an INTERLINK™ Needlefree System available from Baxter, or another similar connector.

In some embodiments, the distal end 26 of the extension tube 24 may be coupled to the proximal end 16 of the catheter adapter 12. In some embodiments, another connector 34 may be configured to couple the distal end 26 of the extension tube 24 to the proximal end 16 of the catheter adapter 12. In some embodiments, the connector 34 may selectively or fixedly couple the distal end 26 of the extension tube 24 to the proximal end of the catheter adapter 12. In some embodiments, the connector 34 may include a luer adapter, such as a male or female luer adapter, or any other suitable connector. In some embodiments, the luer adapter may include a rotating collar luer lock. For example, the luer adapter may include a free rotating collar with threads, and locking may be achieved by rotating the collar.

In some embodiments, the catheter adapter 12 may include a side port and may be integrated, having extension tubing extending from the side port. In some embodiments, the catheter adapter 12 may be straight or non-integrated. As illustrated, for example, in FIGS. 1A-1B, in some embodiments with a straight or non-integrated catheter, the catheter adapter 12 may not include a side port and/or extension tubing extending from the side port the connector 30 may include any suitable septum 38, which may prevent blood and/or other fluid from leaking out of the connector 30 in a proximal direction. In some embodiments, the septum 38 may be single-use or multi-use. In some embodiments, a septum 40 may be disposed within the lumen 18, which may prevent blood and/or other fluid from leaking out of the proximal end 16 of the catheter adapter 12. Additionally, in some embodiments, a septum actuator may be disposed within the lumen 18.

In some embodiments, one or more of the following may form a straight pathway 41 for delivery of an instrument into the catheter system 10 and/or the vasculature: the lumen 18, the catheter 20, the connector 30, the extension tube 24, and the connector 34. In some embodiments, the straight pathway 41 may be aligned with a longitudinal axis 42 of the catheter assembly 22. In some embodiments, the straight pathway 41 may reduce a likelihood of kinking or bending of the instrument. In some embodiments, such as, for example, where the instrument includes tubing for infusion or blood draw, kinking may lead to occlusion, which may slow or stop fluid or blood flow through the tubing. In some embodiments, the straight pathway 41 may be unobstructed.

In some embodiments, the extension tube 24 may be rigid, semi-rigid, or flexible. In some embodiments, the extension tube 24 may allow remote delivery of the instrument, which may decrease disturbance of the insertion site of the catheter. In some embodiments, the extension tube 24 may be a first extension tube. In some embodiments, the catheter system 10 may include a second extension tube 44, which may be coupled to the extension tube 24. In some embodiments, the second extension tube 44 may be disposed at an angle with respect to the extension tube 24.

In some embodiments, a hardness of the extension tube 24 may be greater than a hardness of the second extension tube 44. In some embodiments, the hardness of the extension tube 24 may be less than a hardness of the catheter adapter 12, which may reduce a risk of disturbing an insertion site of the catheter 20. In some embodiments, the extension tube 24 and/or the second extension tube 44 may include a clamp 39. In some embodiments, the second extension tube 44 may be coupled to the straight pathway 41 distal to or proximal to the connector 30.

In some embodiments, the extension tube 24 may include a rigid or semi-rigid portion of the straight pathway 41 there through to facilitate delivery of the instrument into the catheter system 10 and/or the second extension tube 44 may be more flexible or compliant to cause less irritation to the skin of the patient. In some embodiments, the second extension tube 44 may be rigid, semi-rigid, or flexible. In some embodiments, the extension tube 24 may include a durometer between 70 Shore A and 95 Shore A, inclusive. In some embodiments, the extension tube 24 may include a durometer greater than 95 Shore A. In some embodiments, the second extension tube 44 may include a durometer of about 35 Shore A or between 70 Shore A and 95 Shore A, inclusive. In some embodiments, the extension tube may include a length that allows the instrument being placed into the catheter system 10 to reach into the catheter adapter 12, into the catheter 20, and/or beyond the catheter 20 into the vasculature of the patient.

In some embodiments, a proximal end of the second extension tube 44 or an end of the second extension tube 44 opposite an end of the second extension tube 44 coupled to the extension tube 24, may include a connector 46, such as a luer adapter or another suitable connector. In some embodiments, the connector 46 may connect the second extension tube 44 to a blood collection device or infusion means.

In some embodiments, the connector 30 may include a Y-adapter, as illustrated, for example, in FIGS. 1A-1B. In some embodiments, the second extension tube 44 may be coupled to the extension tube 24 via the Y-adapter. In some embodiments, a first port of the Y-adapter may be aligned with the longitudinal axis 42 of the catheter assembly 22. In some embodiments, the second extension tube 44 may extend from a second port of the Y-adapter. In some embodiments, the catheter system 10 may include the extension tube 24 but not the second extension tube 44.

In some embodiments, an extension set 47 for the catheter assembly 22 may include one or more of the following: the extension tube 24, the connector 30 coupled to the proximal end 28 of the extension tube 24, the connector 34 coupled to the distal end 26 of the extension tube 24, the second extension tube 44, and the connector 46. In some embodiments, the extension tube 24, the connector 30, and the connector 34 may form at least a portion of the straight pathway 41.

Figure 1C:
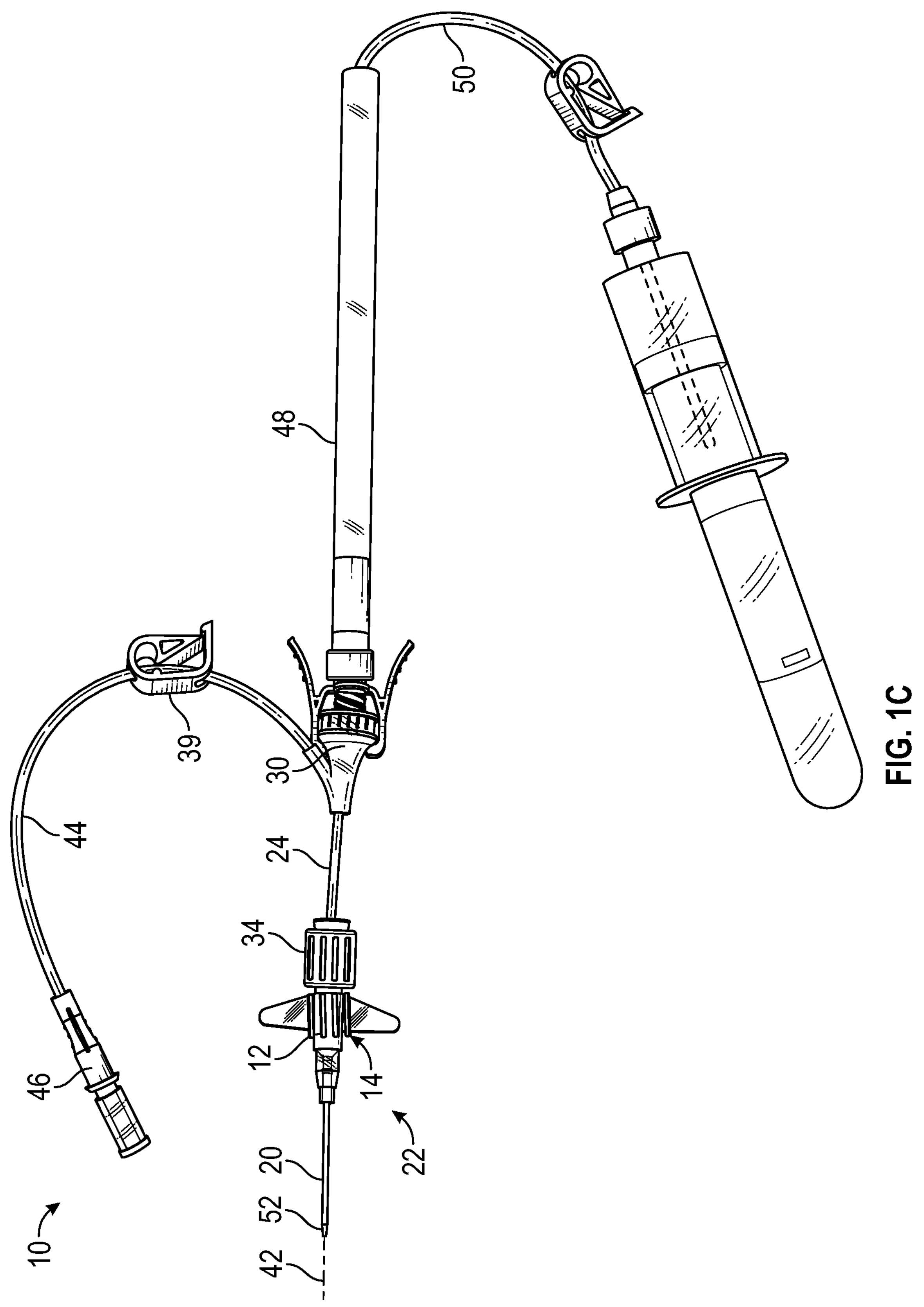
FIG. 1C is an upper perspective view of the catheter system of FIG. 1A coupled with an example instrument delivery device, according to some embodiments.

Referring now to FIG. 1C, in some embodiments, an instrument delivery device 48 may be coupled to the connector 30. In some embodiments, the instrument delivery device 48 may include any type of delivery device capable of being coupled to the connector 30. In some embodiments, the instrument delivery device 48 may include the instrument 50, such as, for example, a guidewire, a probe with a sensor, tubing for fluid infusion or blood draw, a light tube for disinfection, or another suitable instrument. In some embodiments, the instrument 50 may be advanced distally through and/or from the instrument delivery device 48 into the catheter system 10. In some embodiments, a distal end of the instrument 50 may be advanced beyond a distal end 52 of the catheter 20. In some embodiments, the distal end of the instrument 50 may be advanced to a location within the catheter assembly 22 and/or the vasculature. As illustrated in FIG. 1C, in some embodiments, the instrument 50 may include blood draw tubing, which may be coupled to a blood collection device, such as a blood collection tube or adapter for a blood collection tube.

Figure 1D:
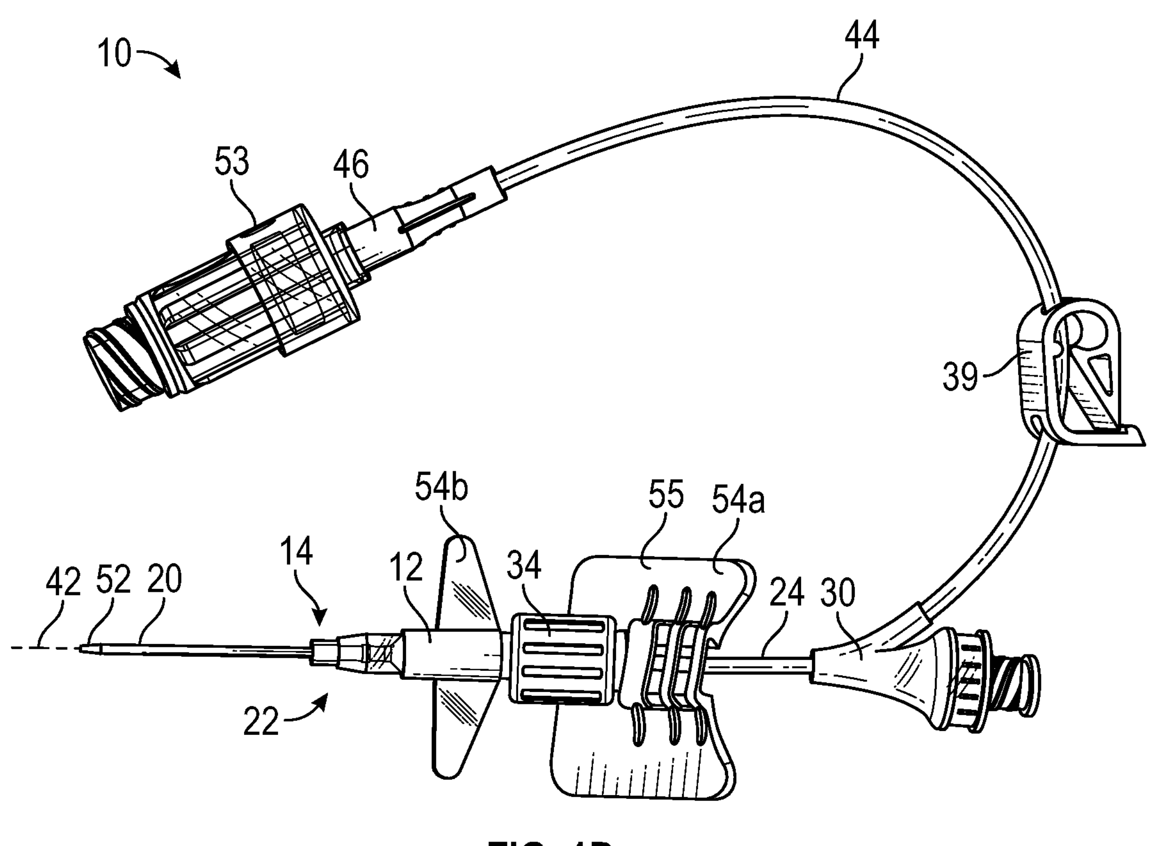
FIG. 1D is an upper perspective view of the catheter system of FIG. 1A, illustrating example stabilization features, according to some embodiments.
Figure 1E:
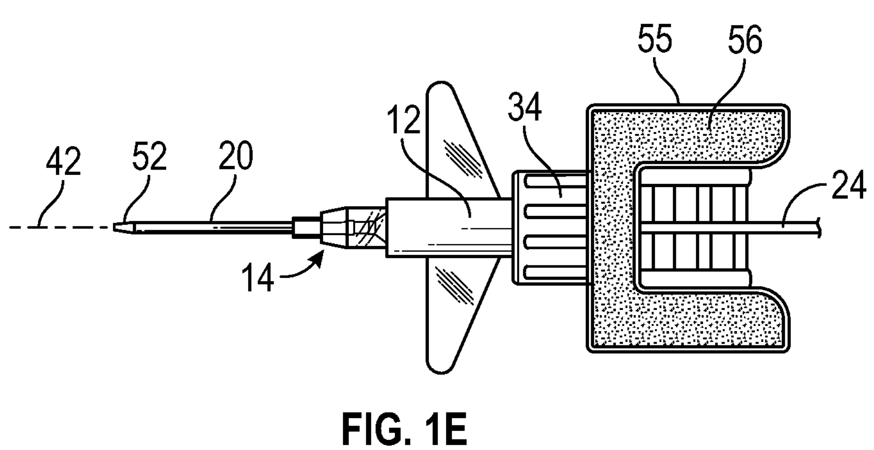
FIG. 1E is a bottom view of a portion of the catheter system of FIG. 1A, illustrating the stabilization features, according to some embodiments.

Referring now to FIG. 1D-1E, in some embodiments, the catheter system 10 may include a stabilization feature 54. In some embodiments, the stabilization feature 54 may be disposed between the connector 30 and the distal end 26 of the extension tube 24. In some embodiments, the extension tube 24 may extend through the stabilization feature 54.

In some embodiments, the stabilization feature 54 may include one or more platforms 55, which may be configured to contact the skin of the patient. In some embodiments, a particular platform 55 may include one or more wings. In some embodiments, a particular platform 55 may extend on both sides of the longitudinal axis 22 and/or may include two generally parallel arms joined by a connector portion, as illustrated, for example, in FIG. 1E.

In some embodiments, the stabilization feature 54 may be fixed with respect to the extension tube 24. In some embodiments, the stabilization feature 54 may rotate on the extension tube 24 about the longitudinal axis of the extension tube 24. In some embodiments, the stabilization feature 54 may be integrally formed with the extension tube 24. In some embodiments, the stabilization feature 54 may be a separate piece from the extension tube 24. In some embodiments, the stabilization feature 54 may snap onto the extension tube 24.

In some embodiments, the stabilization feature 54 may stabilize the extension tube 24 and/or extension set 47 during insertion of the instrument 50 through the extension tube 24. In some embodiments, one or more digits of a user may grip or contact an upper surface of the platform 55 to stabilize the catheter system 10 during insertion of the instrument 50 through the extension tube 24.

In some embodiments, the stabilization feature 54 may be disposed on the connector 30 or the connector 34. In some embodiments, the stabilization feature 54 may be fixed with respect to the connector 30 and/or the connector 34. In some embodiments, the stabilization feature 54 may rotate on the connector 30 and/or the connector 34. In some embodiments, the stabilization feature 54 may be monolithically formed as a single unit or integrally formed with the connector 30 and/or the connector 34. In some embodiments, the stabilization feature 54 may be a separate piece from the connector 30 and/or the connector 34. In some embodiments, the stabilization feature 54 may snap onto the connector 30 and/or the connector 34. In some embodiments, the stabilization feature 54 and/or the catheter system 10 may be low-profile.

In some embodiments, the catheter system 10 may include multiple stabilization features 54. In some embodiments, the catheter system 10 may include a stabilization feature 54 on one or more of the catheter adapter 12, the connector 30, the connector 34, and the extension tube 24. FIG. 1D illustrates a first stabilization feature 54*a* and a second stabilization feature 54*b*. In some embodiments, the first stabilization feature 54*a* may be disposed between the connector 30 and the distal end 26 of the extension tube (illustrated in FIG. 1B, for example. In some embodiments, the second stabilization feature 54*b* may be disposed on the catheter adapter 12. The first stabilization feature 54*a* and the second stabilization feature 54*b* may be referred to collectively in the present disclosure as "stabilization feature 54." In some embodiments, a needleless connector 53 may be coupled to one or more of the connectors 30, 34, and 46. In some embodiments, a particular needleless connector 53 may be disposed between the connector 30 and the instrument delivery device 48. In some embodiments, a particular needleless connector 53 may be disposed between the connector 34 and the proximal end of the catheter adapter 12.

In some embodiments, the platforms 55 may each include an adhesive layer 56, which may be configured to contact the skin of the patient. In some embodiments, the adhesive layer 56 may be covered by a removable backing layer, which may be removed prior to securing the stabilization feature 54 to the patient.

Figures 1F, 1G:
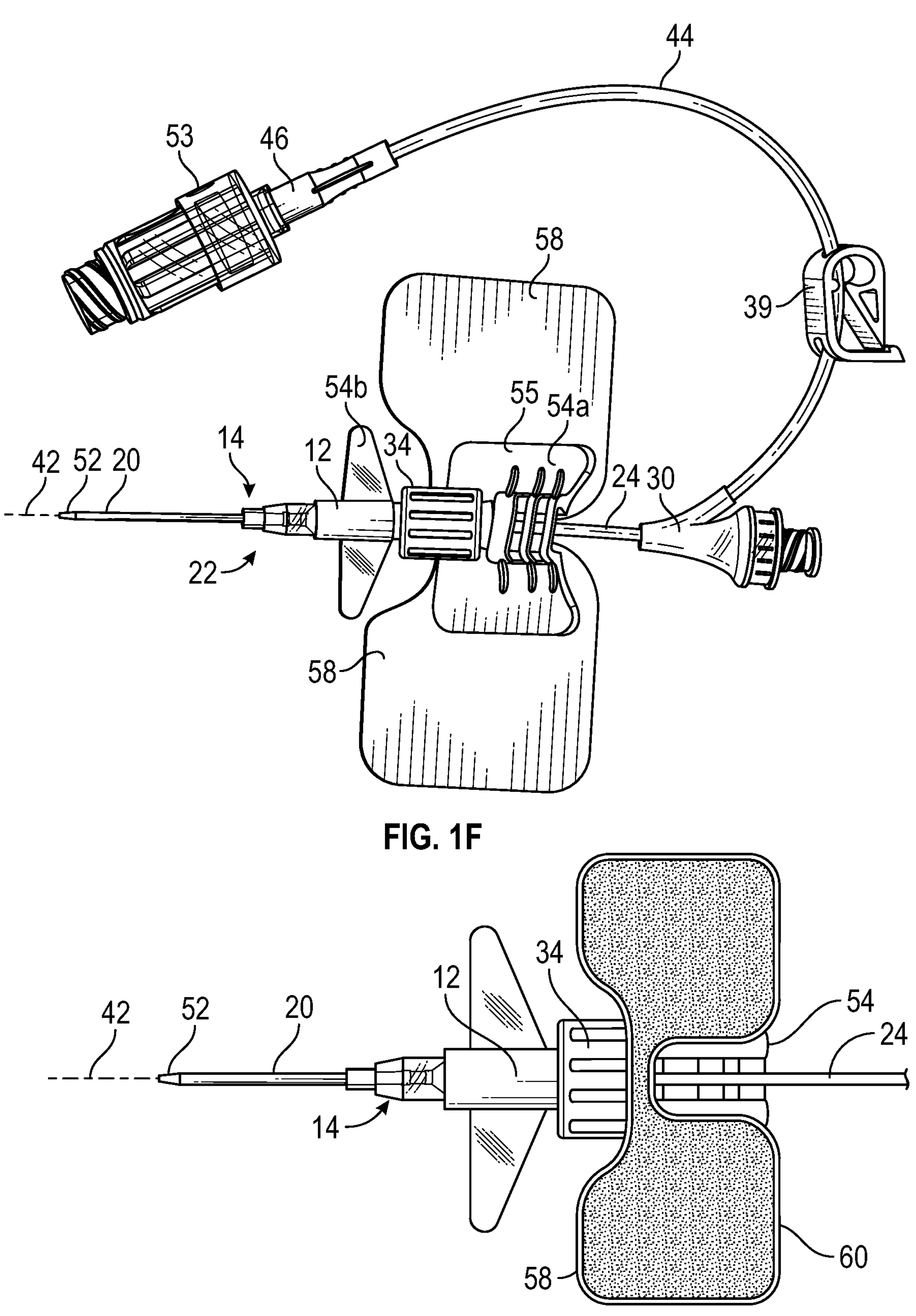
FIG. 1F is an upper perspective view of the catheter system of FIG. 1A, illustrating example securement fabric, according to some embodiments.
FIG. 1G is a bottom view of a portion of the catheter system of FIG. 1A, illustrating the securement fabric, according to some embodiments.

Referring now to FIGS. 1F-1G, in some embodiments, the catheter system 10 may include securement fabric 58, which may be coupled to and/or extend underneath of the stabilization feature 54, such as, for example, the platforms 55. In some embodiments, the fabric 58 may extend outwardly from the platforms 55 or away from the longitudinal axis of the extension tube 24. In some embodiments, the fabric 58 may include an adhesive layer 60, which may be configured to contact the skin of the patient. In some embodiments, the adhesive layer 60 may be covered by a removable backing layer, which may be removed prior to securing the stabilization feature 54 to the patient.

Figure 1H:
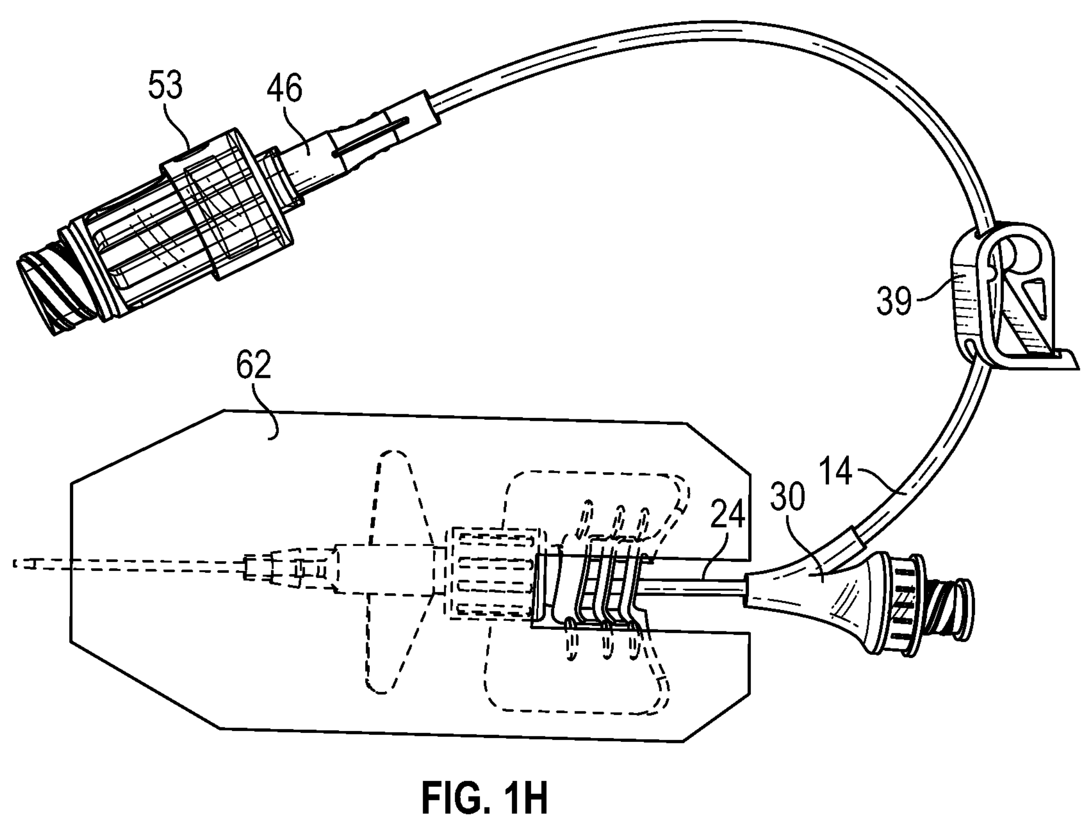
FIG. 1H is an upper perspective view of the catheter system of FIG. 1A, illustrating an example dressing, according to some embodiments.
Figure 1I:
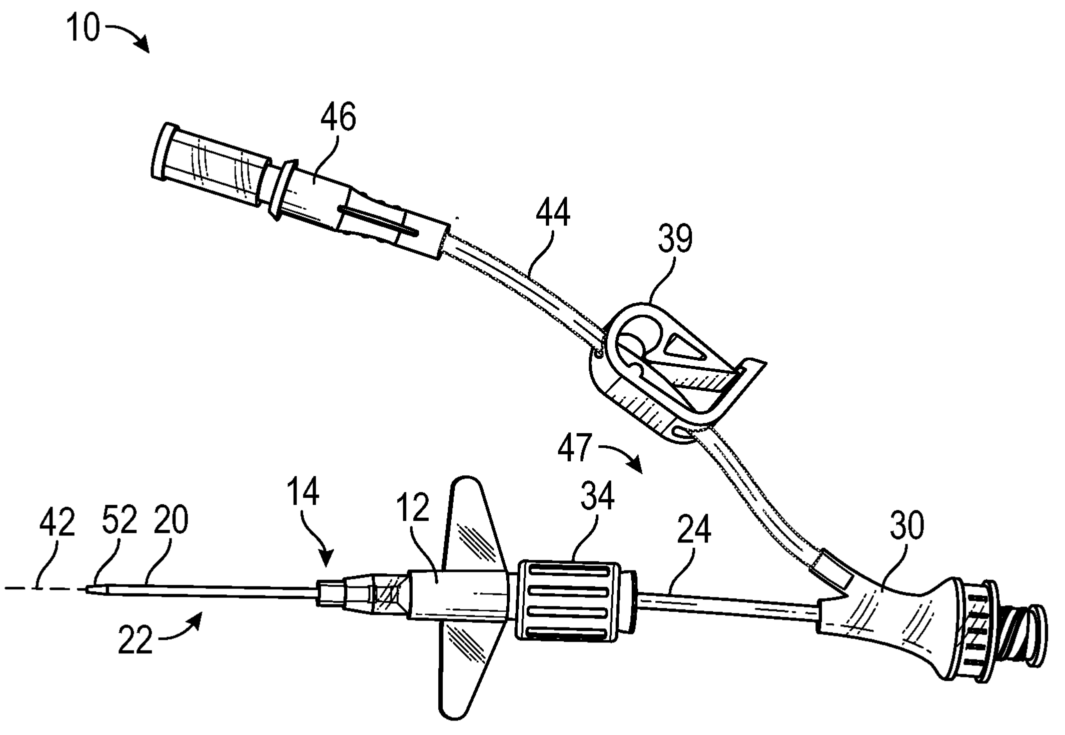
FIG. 1I is an upper perspective view of the catheter system of FIG. 1A, illustrating an example connector having a distally oriented port, according to some embodiments.

Referring now to FIG. 1H, in some embodiments, the catheter system 10 may include a dressing 62. In some embodiments, the dressing 62 may be disposed on top of the securement feature 54 and/or fabric 58. The dressing 62 may be used to secure the catheter system 10 and/or prevent contamination or infection. In some embodiments, the dressing 62 may help stabilize or secure the securement feature 54, the fabric 58, and/or the catheter system 10 in addition to or as an alternative to the adhesive layer 56 and/or the adhesive layer 60. In some embodiments, the dressing 62 may include a slit or slot aligned with the extension tube 24, which may allow access to the connector 30 and some movement of the extension tube 24 without providing directed leverage on the catheter adapter 12 the insertion site of the catheter 20.

Referring now to FIG. 1H, in some embodiments, the second extension tube 44 may be disposed at an angle with respect to the extension tube 24. As illustrated in FIG. 1H, in some embodiments, a port of the connector 30 and the second extension tube 44 may be distally oriented or facing. In other embodiments, as illustrated in FIG. 1A, for example, the port of the connector 30 and the second extension tube 44 may be proximally oriented or facing. In other embodiments, the port of the connector 30 and the second extension tube 44 may be perpendicular with respect to the catheter adapter 12.

Figure 1J:
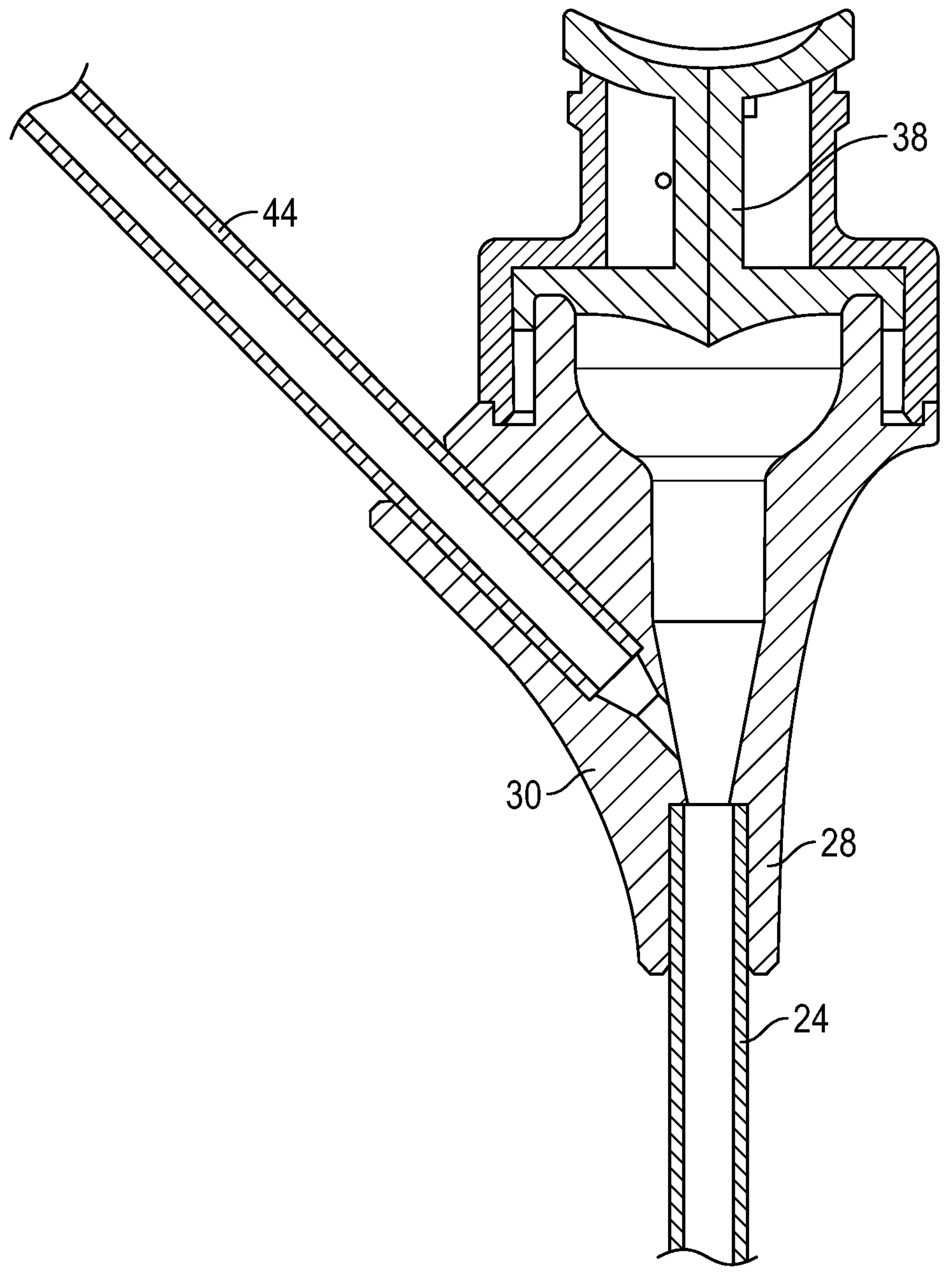
FIG. 1J is a cross-sectional view of an example connector coupled to a proximal end of an example extension tube, according to some embodiments.

Referring now to FIG. 1J, in some embodiments, a portion of the straight pathway 41 extending through the connector 30 and/or the extension tube 24 may be smooth such that the instrument 50 is prevented from disturbance by any catches, such as any sharp edges or snag points, within the connector 30. In some embodiments, an entirety of the straight pathway 41 may be smooth without any catches so as to allow the instrument to be smoothly advanced in a distal direction through the straight pathway 41 and/or smoothly retracted in a proximal direction through the straight pathway 41. In some embodiments, any catches disposed within the connector 30 and/or at a transition between the connector 30 and the extension tube 24 may be positioned behind smooth features and geometry to prevent the instrument 50 from getting caught or snagged.

In further detail, in some embodiments, an inner surface of the connector 30 may form a portion of the straight pathway 41. In some embodiments, a portion of the inner surface of the connector 30 proximate and proximal to the proximal end 28 of the extension tubing 28 may be even with or extend more inwardly than an inner surface of the extension tube 24. This may prevent the instrument 50 from getting caught on the proximal end 28 of the extension tube 24 when the instrument 50 is advanced in the distal direction. In some embodiments, an inner surface of the proximal end 28 of the extension tubing 24 may be disposed an equal distance from or further from a longitudinal axis of the connector 30 as the portion of the inner surface of the connector 30 proximate and proximal to the proximal end 28 of the extension tubing 24. In some embodiments, an inner diameter of the straight pathway 41 proximate and proximate to the proximal end 28 of the extension tube 24 may be approximately equal to or less than an inner diameter of the extension tube 24.

Figure 2A:
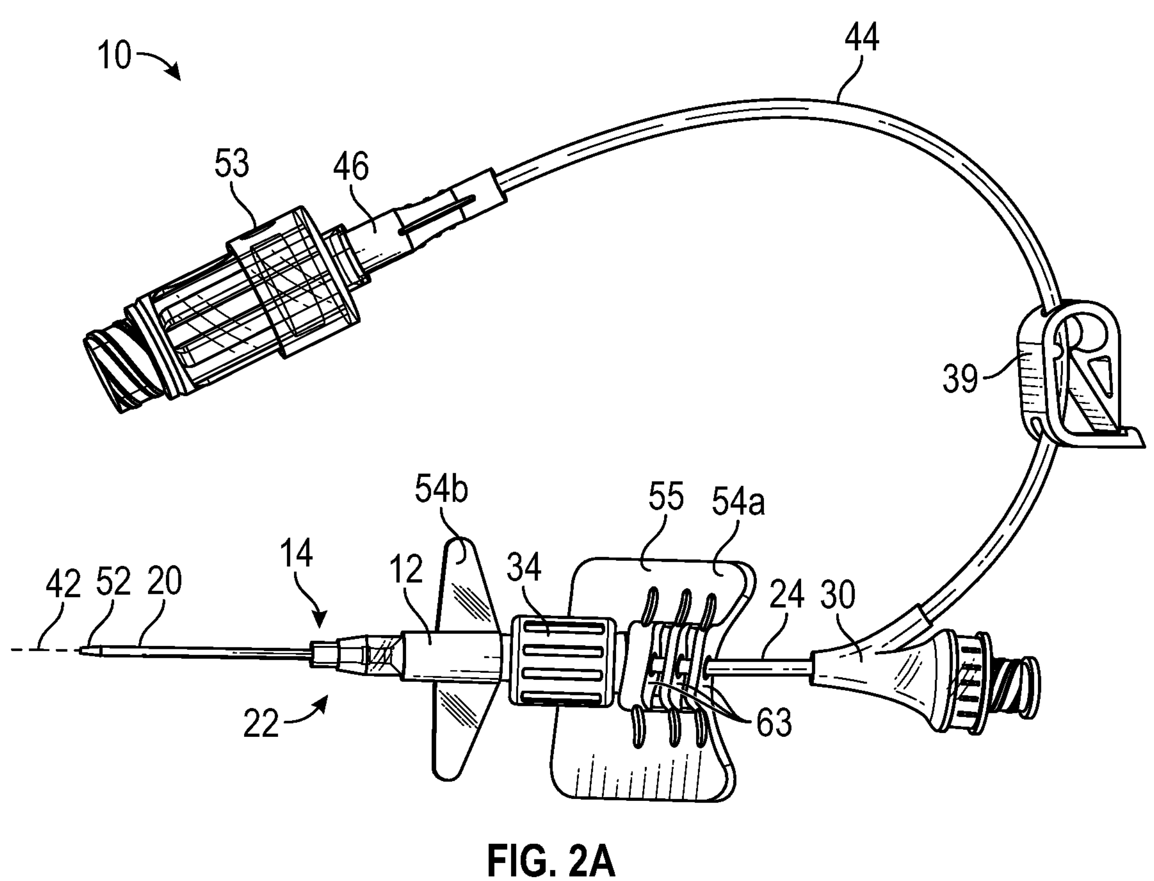
FIG. 2A is an upper perspective view of the catheter system of FIG. 1A, illustrating another example stabilization feature, according to some embodiments.
Figure 2B:
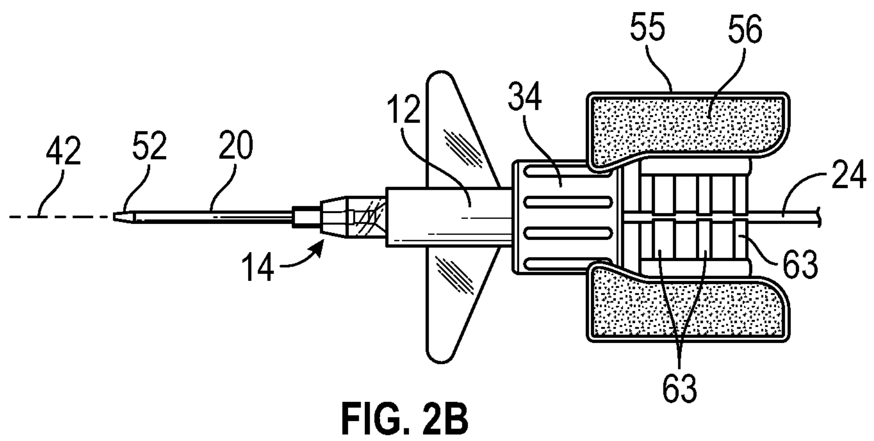
FIG. 2B is a bottom view of a portion of the catheter system of FIG. 1A, illustrating the other stabilization feature, according to some embodiments.

Referring now to FIGS. 2A-2B, in some embodiments, the stabilization feature 54 may include one or more snap features 63, which may allow the stabilization feature 54 to snap onto the extension tube 24.

Figure 2C:
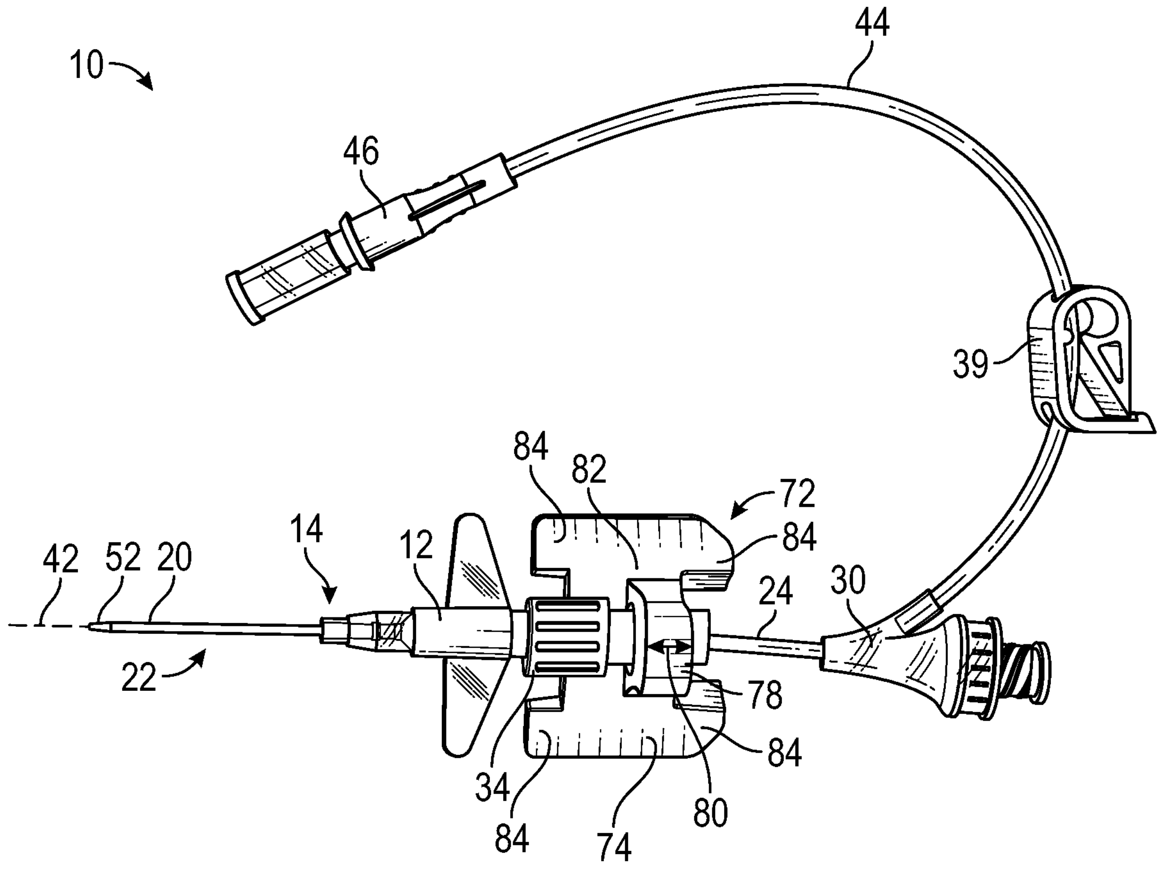
FIG. 2C is an upper perspective view of the catheter system of FIG. 1A, illustrating another example stabilization feature, according to some embodiments.
Figure 2D:
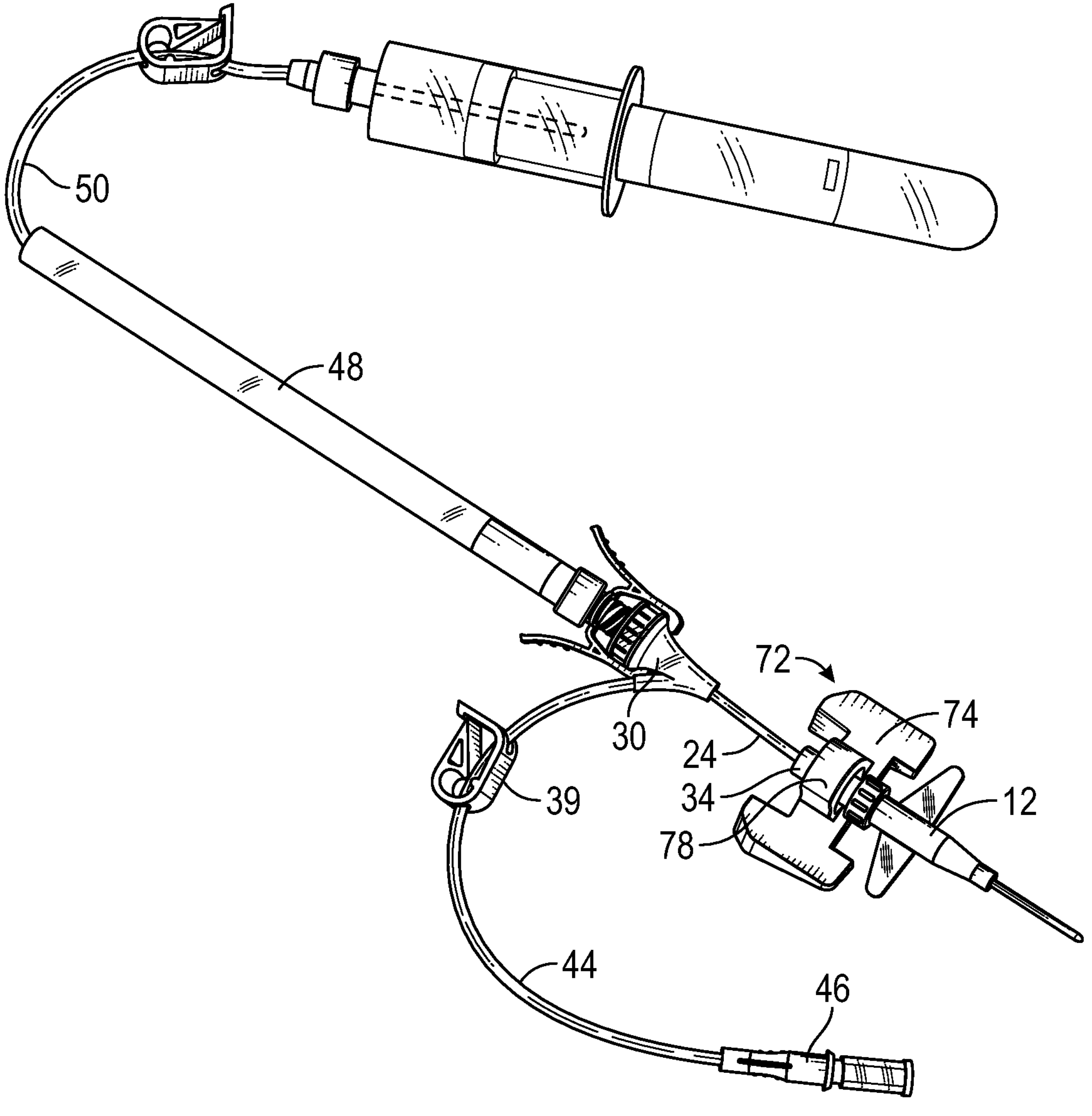
FIG. 2D is an upper perspective view of the catheter system of FIG. 1A, illustrating the stabilization feature of FIG. 2C, according to some embodiments.
Figure 2E:
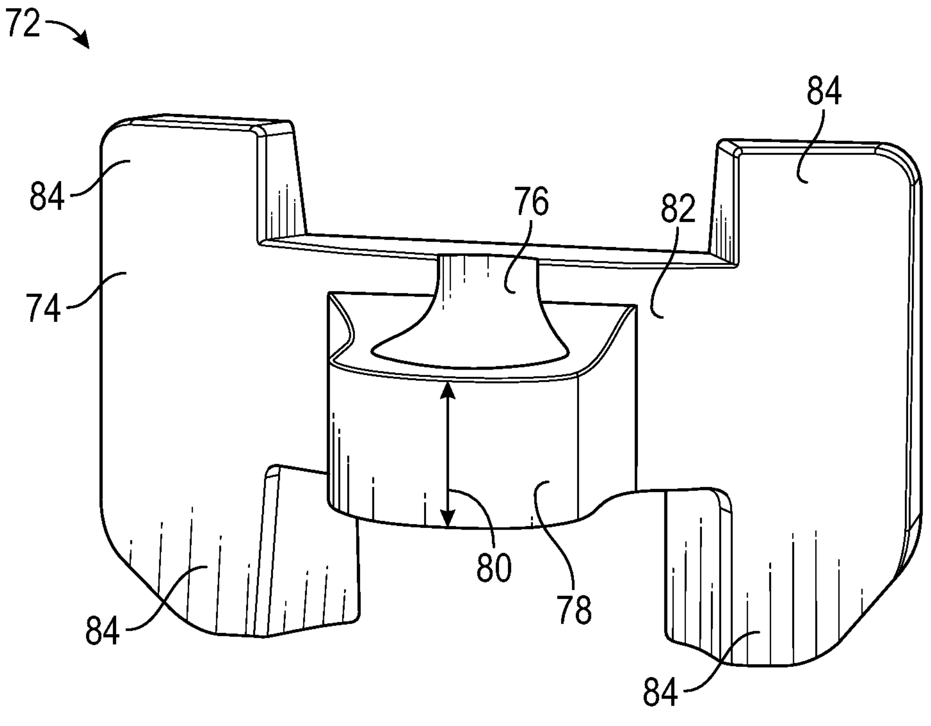
FIG. 2E is an upper perspective view of the stabilization feature of FIG. 2C, according to some embodiments.

Referring now to FIGS. 2C-2E, a stabilization feature 72 is illustrated, according to some embodiments. In some embodiments, the stabilization feature 72 may include or correspond to the connector support device described in U.S. Pat. No. 11,497,891, granted Nov. 15, 2022, entitled "VASCULAR ACCESS CONNECTOR SUPPORT DEVICE, SYSTEMS, AND METHODS," which is hereby incorporated by reference in its entirety.

In some embodiments, the stabilization feature 72 may be wedge-shaped, which may facilitate support of the connector 34 at an insertion angle of the catheter 20 into the patient. In further detail, in some embodiments, an upper surface 74 of the stabilization feature 72 may include a groove 76, which may be aligned with a longitudinal axis of the catheter 20. In some embodiments, the connector 34 may rest within the groove 76. In some embodiments, a thickness of the stabilization feature 72 at a proximal end of the groove 76 may be greater than a thickness of the stabilization feature 72 at a distal end of the groove 76 such that groove 76 may support the connector 34 at the insertion angle. In some embodiments, the insertion angle may be about 30° or less. In some embodiments, the insertion angle may be between 0° and 40°. Thus, in some embodiments, stabilization feature 72 may include a wedge-shape with an angle about 30° or less or between 0° and 40°.

In some embodiments, the connector 34 may extend into and/or through a ring 78 of the stabilization feature 72, which may extend from the upper surface 74. In some embodiments, a distal end of the connector 34 may include the luer adapter, which may include the rotating collar luer lock. In some embodiments, the rotating collar luer lock, which may be threaded, may be disposed distal to the ring 78 for easy access and rotation by the clinician. In some embodiments, a portion of the connector 34 proximal to the rotating collar luer lock may extend into and/or through the ring 78 of the stabilization feature 72. In some embodiments, an outer surface of the rotating collar luer lock may include one or more ribs to facilitate tightening or loosening of the rotating collar luer lock by the clinician.

In some embodiments, the ring 78 may contact the connector 34 and hold the connector 34 snugly in place. In some embodiments, a width 80 of the ring 78 may extend along all or a portion of a bridge 82, which may facilitate securement of the connector 34. In some embodiments, the bridge 82 may join four leg portions 84 of an H-shape of the stabilization feature 72. In some embodiments, the stabilization feature 72 may not include protrusions on the upper surface 74, which might otherwise contact and support a port or extension tube.

Referring now to FIGS. 3A-3D, another catheter system 64 is illustrated. In some embodiments, the catheter system 64 may include or correspond to the catheter system 10 of FIG. 1. In further detail, the catheter system 64 may include one or more features of the catheter system 10. As an example, the catheter system 64 may include one or more of the following: the stabilization feature 54, the fabric 58, the second extension tube 44, and the connector 30. Similarly, in some embodiments, the catheter system 10 may include one or more features of the catheter system 64.

Figure 3A:
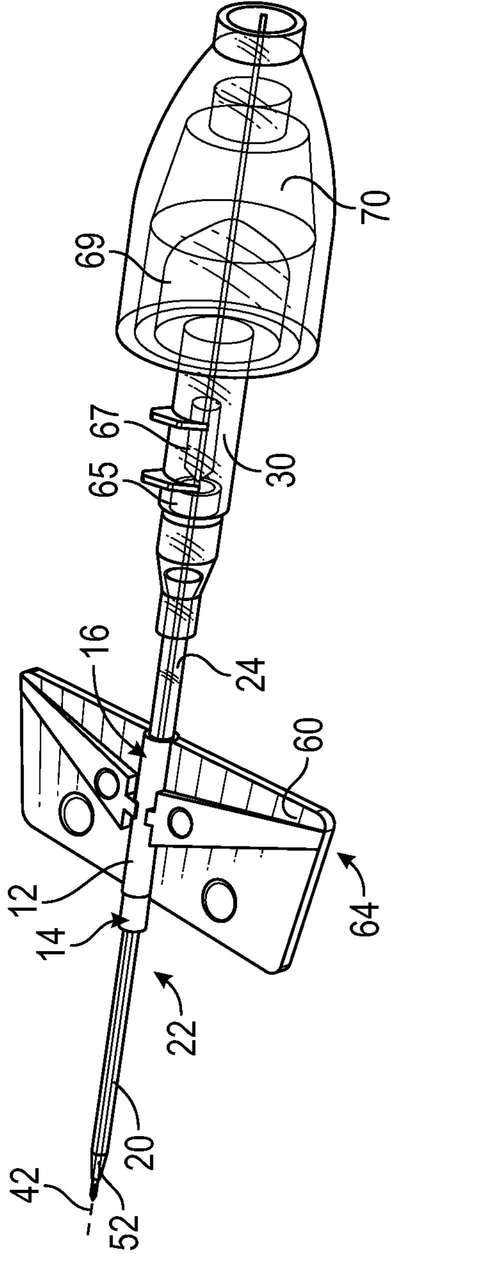
FIG. 3A is an upper perspective view of another catheter system, illustrating an example connector having an example septum and example septum actuator, according to some embodiments.

In some embodiments, the connector 30 may include a luer adapter. Referring now to FIG. 3A, in some embodiments, the connector 30 may optionally include a blood control mechanism, such as, for example, blood control septum 65. In some embodiments, the connector 40 may include a septum actuator 67, which may penetrate the septum 65 in response to insertion of a luer device.

In some embodiments, a proximal end of a needle 68 may be secured in a needle hub 70. In some embodiments, the catheter system 64 may include any suitable needle safety or shield mechanism 69. In some embodiments, the safety mechanism 69 may be disposed in and/or selectively coupled to the needle hub 70, the catheter 12, and/or the connector 30. In some embodiments, the safety mechanism 69 may be disposed in and/or selectively coupled to another connector, such as a needleless connector, which may be positioned between the connector 30 and the needle hub 70.

The safety mechanism 69 may be coupled or selectively coupled with the catheter system 64 in any number of ways. For example, the safety mechanism 69 may include an external interlock (for example, similar to the BD NEXIVA™ Closed IV Catheter System) or an internal interlock. In some embodiments, the safety mechanism 69 may be active (for example, similar to the BD INSYTE™ AUTOGUARD™ BC Shielded IV Catheter) or passive. In some embodiments, the safety mechanism 69 may encapsulate a sharp distal tip of the needle 68 in response to proximal withdrawal of the needle 68 (for example, similar to the BD SAF-T-INTIMA™ Closed IV Catheter System).

Figure 3B:
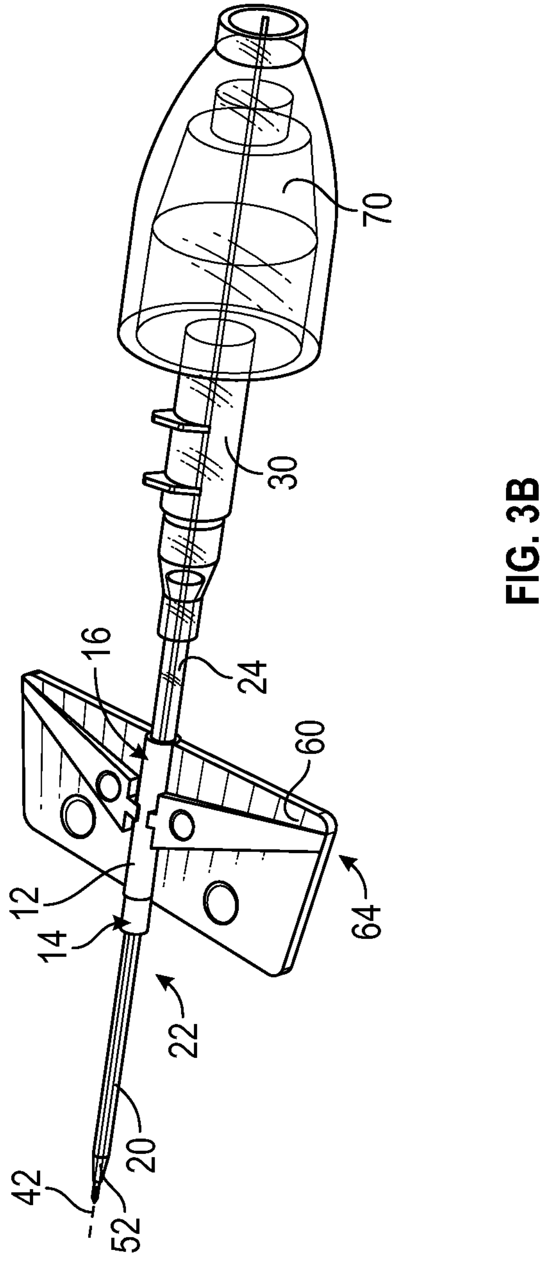
FIG. 3B is an upper perspective view of the catheter system of FIG. 3A, having an example clip and without the septum and the actuator, according to some embodiments.
Figures 3C, 3D:
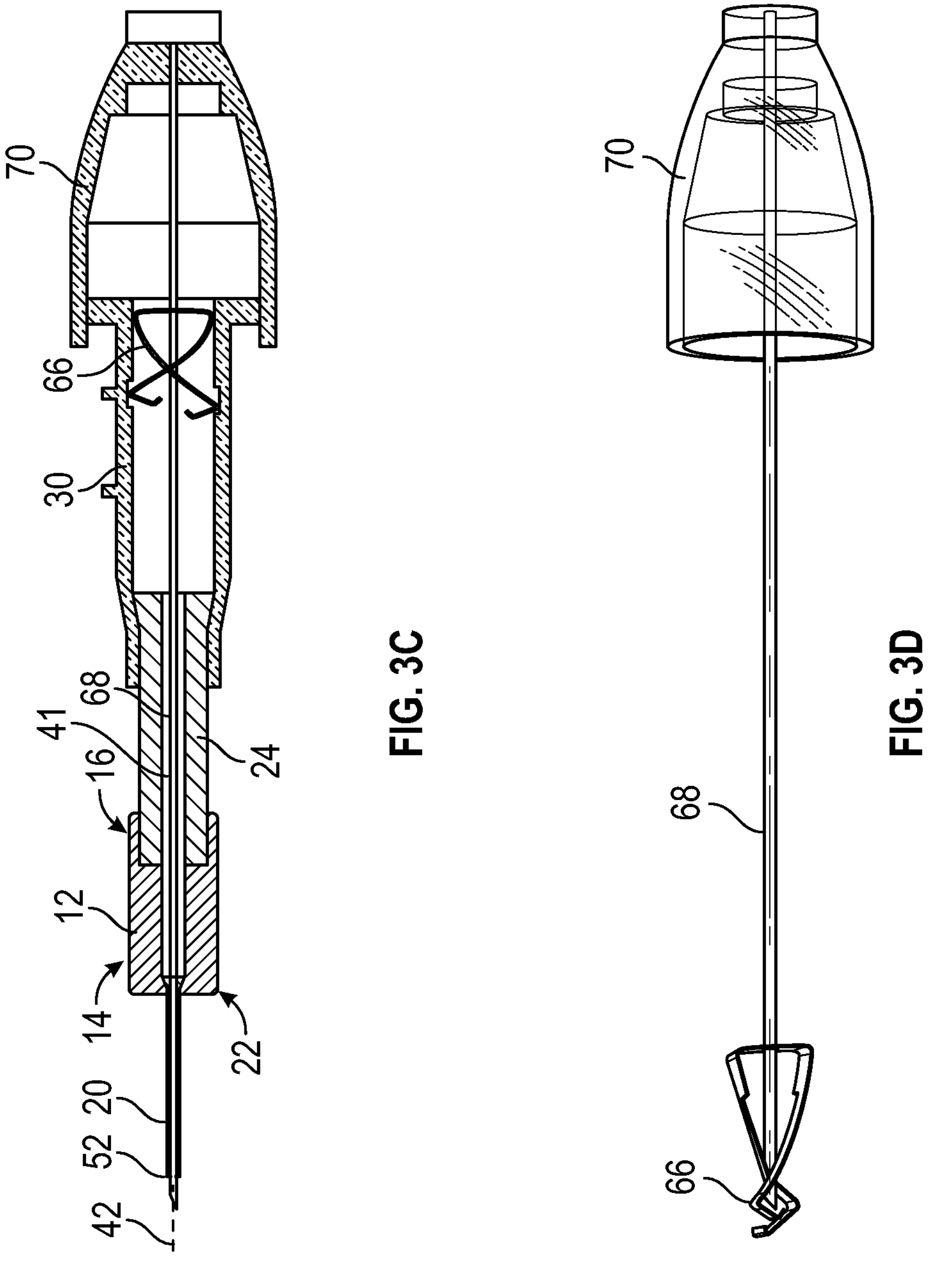
FIG. 3C is a cross-sectional view of the catheter system of FIG. 3A, having the clip and without the septum and the actuator, according to some embodiments.
FIG. 3D is an upper perspective view of an example needle shielding mechanism, according to some embodiments.

Referring now to FIGS. 3B-3D, a clip 66, which is an example of a safety mechanism having an internal interlock, is illustrated, according to some embodiments. Although the septum 65 and septum actuator 67 are not illustrated in FIGS. 3B-3D, it is understood that the connector 30 may include one or more of the following: the septum 65, the septum actuator 67, and the clip 66. In some embodiments, in response to the needle 68 being proximally withdrawn from the catheter adapter 12, a sharp distal tip of the needle 68 may be shielded in the clip 66 and the clip 66 may be uncoupled and removed from the catheter system 64. In some embodiments, the clip 66 may be disposed within and/or selectively coupled to the catheter adapter 12. In some embodiments, the clip 66 may be disposed within and/or selectively coupled to the connector 30. In some embodiments, the instrument delivery device 48 may be coupled to the connector 30 after the needle 68 is removed from the catheter system 64.

Referring now to FIGS. 3A-3D, in some embodiments, the extension tube 24 may be pre-attached to the catheter adapter 12. In these and other embodiments, the distal end 26 of the extension tube 24 may be fixedly coupled to or integrated with the proximal end of the catheter adapter 12, as illustrated, for example, in FIGS. 3A-3D. In some embodiments, the distal end 26 of the extension tube 24 may be disposed within the catheter adapter 12.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter system, comprising:

a catheter adapter having a distal end, a proximal end axially aligned with the distal end, and a lumen extending between the distal end and the proximal end;

a catheter extending distally from the distal end of the catheter adapter;

a first flexible extension tube having a distal end and a proximal end, wherein the distal end of the first flexible extension tube is coupled to the proximal end of the catheter adapter;

a first connector coupled to the proximal end of the first flexible extension tube;

a second connector coupled to the distal end of the first flexible extension tube, wherein the first connector, the second connector, the first flexible extension tube, the lumen, and the catheter form a straight pathway for delivery of an instrument to the catheter system; and a stabilization feature disposed on the first flexible extension tube between the first connector and the second connector and adjacent the second connector such that a distal portion of the first flexible extension tube extends through the stabilization feature and a proximal portion of the first flexible extension tube is positioned proximally to and outside of the stabilization feature, wherein the stabilization feature comprises opposing platforms, wherein each of the opposing platforms comprises an adhesive layer configured to contact skin of a patient such that the stabilization feature is configured to inhibit flexing of the distal portion of the first flexible extension tube relative to the second connector while permitting flexing of the proximal portion of the first flexible extension tube as the instrument is delivered to the catheter system through the straight pathway.

2. The catheter system of claim 1, wherein the distal end of the first flexible extension tube is fixedly integrated with the second connector, wherein the second connector comprises a luer adapter threaded to the proximal end of the catheter adapter, wherein the proximal end of the first flexible extension tube is fixedly integrated with the first connector.

3. The catheter system of claim 1, wherein the second connector comprises a luer adapter, wherein the luer adapter is selectively coupled to a corresponding luer adapter disposed on the proximal end of the catheter adapter.

4. The catheter system of claim 1, wherein the catheter system further comprises a second flexible extension tube coupled to the first flexible extension tube, wherein the second flexible extension tube extends from the first connector and is disposed at an angle with respect to the first flexible extension tube.

5. The catheter system of claim 4, wherein the distal end of the first flexible extension tube is fixedly integrated with the second connector threaded to the proximal end of the catheter adapter, wherein the proximal end of the first flexible extension tube is fixedly integrated with the first connector, wherein a distal end of the second flexible extension tube is fixedly integrated with the first connector.

6. The catheter system of claim 4, wherein the first connector comprises a Y-adapter having a first port and a second port, wherein the first port is configured to couple with an instrument delivery device, wherein the second flexible extension tube extends from the second port of the Y-adapter.

7. The catheter system of claim 1, wherein the first connector comprises a blood control septum.

8. The catheter system of claim 1, wherein the first connector is removably coupled to the proximal end of the first flexible extension tube.

9. The catheter system of claim 1, wherein the straight pathway comprises a uniform diameter along an entirety of a length of the straight pathway.

10. A catheter system, comprising:

a catheter adapter having a distal end, a proximal end axially aligned with the distal end, and a lumen extending between the distal end and the proximal end;

a catheter extending distally from the distal end of the catheter adapter;

a first extension tube having a distal end and a proximal end, wherein the distal end of the first extension tube is coupled to the proximal end of the catheter adapter;

a first connector coupled to the proximal end of the first extension tube;

a second connector coupled to the distal end of the first extension tube, wherein the first connector, the second connector, the first extension tube, the lumen, and the catheter form a straight pathway for delivery of an instrument to the catheter system;

a stabilization feature disposed on the first extension tube between the first connector and the second connector, wherein the stabilization feature comprises opposing platforms, wherein each of the opposing platforms comprises an adhesive layer configured to contact skin of a patient; and a second extension tube coupled to the first extension tube, wherein the second extension tube extends from the first connector and is disposed at an angle with respect to the first extension tube;

wherein the distal end of the first extension tube is fixedly integrated with the second connector threaded to the proximal end of the catheter adapter, wherein the proximal end of the first extension tube is fixedly integrated with the first connector, wherein a distal end of the second extension tube is fixedly integrated with the first connector, wherein a hardness of the proximal end of the first extension tube fixedly integrated with the first connector is greater than a hardness of the distal end of the second extension tube fixedly integrated with the first connector.

11. The catheter system of claim 10, wherein the first connector comprises a Y-adapter having a first port and a second port, wherein the first port is configured to couple with an instrument delivery device, wherein the second extension tube extends from the second port of the Y-adapter.

12. The catheter system of claim 10, wherein the first connector comprises a blood control septum.

13. The catheter system of claim 10, wherein the first connector is removably coupled to the proximal end of the first extension tube.

14. The catheter system of claim 10, wherein the straight pathway comprises a uniform diameter along an entirety of a length of the straight pathway.

* * * * *